(12) United States Patent
Delorme et al.

(10) Patent No.: US 6,376,534 B1
(45) Date of Patent: Apr. 23, 2002

(54) COMPOUNDS USEFUL IN PAIN MANAGEMENT

(75) Inventors: Daniel Delorme, Quebec (CA); Vlad Gregor, San Diego, CA (US); Edward Roberts, Solothurn (CH); Eric Sun, San Diego, CA (US)

(73) Assignee: Astrazeneca Canada Inc., Ontario (CA)

( * ) Notice: Subject to any disclaimer, the term of this patent is extended or adjusted under 35 U.S.C. 154(b) by 0 days.

(21) Appl. No.: 09/555,579

(22) PCT Filed: Jun. 16, 1999

(86) PCT No.: PCT/SE99/01076

§ 371 Date: Jun. 1, 1999

§ 102(e) Date: Jun. 1, 1999

(87) PCT Pub. No.: WO99/67205

PCT Pub. Date: Dec. 29, 1999

(30) Foreign Application Priority Data

Jun. 22, 1998 (SE) ................................................ 9802207

(51) Int. Cl.[7] ................... A61K 31/155; C07D 211/01; C07D 333/54

(52) U.S. Cl. ..................... 514/443; 424/1.81; 424/1.85; 424/1.89; 514/634; 549/58; 564/316

(58) Field of Search .................... 564/316; 424/1.81, 424/1.85, 1.89; 549/58; 514/443, 634

(56) References Cited

U.S. PATENT DOCUMENTS

| | | | |
|---|---|---|---|
| 5,710,130 A | | 1/1998 | Schacht et al. ................ 514/19 |
| 5,834,468 A | * | 11/1998 | Breault et al. ............... 514/247 |

FOREIGN PATENT DOCUMENTS

| | | | |
|---|---|---|---|
| EP | 271 829 | 6/1988 | .......... C07C/123/00 |
| WO | WO 98/07420 | 2/1998 | .......... A61K/31/34 |

OTHER PUBLICATIONS

Takemori, et al., "Selective Natrexone–Derived Opioid Receptor Antagonists," *Annu. Rev. Pharmacol. Toxicol.* 32:239–269 (1992).
International Search Report for PCT/SE99/01076, Sep. 18, 2000.

* cited by examiner

Primary Examiner—T. A. Solola
Assistant Examiner—Sonya Wright
(74) Attorney, Agent, or Firm—Pillsbury Winthrop LLP

(57) ABSTRACT

Compounds of general formula I

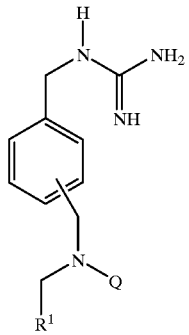

are disclosed and claimed in the present application, as well as their pharmaceutically acceptable salts, pharmaceutical compositions comprising the novel compounds and their use in therapy, in particular in the management of pain. Intermediates to the compounds of the formula I are also claimed.

10 Claims, No Drawings

COMPOUNDS USEFUL IN PAIN MANAGEMENT

CROSS REFERENCE TO RELATED APPLICATIONS

The present application represents U.S. national stage of international application PCT/SE99/01076 which has an international filing date of Jun. 16, 1999 and which was published in English under PCT Article 21(2) on Dec. 29, 1999. The international application claims priority to Swedish application 9802207-2, filed oil Jun. 22, 1998.

FIELD OF THE INVENTION

The present invention is related to novel compounds, to a process for their preparation, their use and pharmaceutical compositions comprising the novel compounds. Also intermediates to the compounds of the present application are claimed. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269. for review). These compounds, e.g. naltrindole, suffer from rather poor (i.e., <10-fold) selectivity for the δ receptor vs. $\mu$ receptor binding and exhibit no analgesic activity, a fact which underscores the need for the development of highly selective non-peptidic δ ligands.

Thus, the problem underlying the present invention was to find new analgesics having improved analgesic effects, but also with an improved side-effect profile over current $\mu$ agonists and potential oral efficacy.

Analgesics that have been identified and are existing in the prior art have many disadvantages in that they suffer from poor pharmacokinetics and are not analgesic when administered by systemic routes. Also, it has been documented that preferred compounds, described within the prior art, show significant convulsive effects when administered systemically.

The problem mentioned above has now been solved by developing novel substituted phenyl compounds, as will be described below.

OUTLINE OF THE INVENTION

The novel compounds according to the present invention are defined by the general formula I

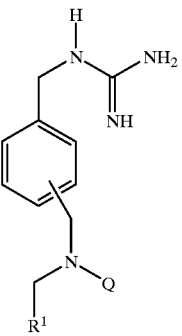

wherein
R$^1$ is selected from anyone of
(i) a straight or branched C$_1$–C$_6$ alkyl, C$_2$–C$_6$ alkenyl or C$_2$–C$_6$ alkynyl, where each alkyl, alkenyl or alkynyl may optionally be substituted by one or more aromatic or heteroaromatic substituents;
(ii) C$_3$–C$_7$ cycloalkyl optionally substituted by anyone of C$_1$–C$_6$ alkyl, C$_1$–C$_6$ alkoxy, or hydroxy;
(iii) hydrogen, halogen or C$_1$–C$_6$ alkoxy;
(iv) C$_6$–C$_{10}$ aryl;
(v) heteroaryl having from 5 to 10 atoms and the heteroatom being selected from any of S, N and O; wherein the aryl and heteroaryl may optionally and independently be substituted by 1 or 2 substituents Y wherein each Y is as defined below;

Q is selected from any of CH$_3$;

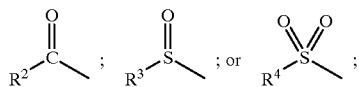

wherein
R$^2$, R$^3$ and R$^4$ is each and independently selected from any of
(i) C$_6$–C$_{10}$ aryl; or
(ii) heteroaryl having from 5 to 10 atoms and the heteroatom being selected from any of S, N and O; and
wherein the aryl and heteroaryl may optionally and independently be substituted by 1 or 2 substituents Y where each Y is as defined below;
(iii) hydrogen;
(iv) a straight or branched C$_1$–C$_6$ alkyl, C$_2$–C$_6$ alkenyl or C$_2$–C$_6$ alkynyl;
(v) saturated or unsaturated C$_3$–C$_{10}$ cycloalkyl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;
Y is each and independently selected from any of hydrogen, CH$_3$; —(CH$_2$)$_{p1}$CF$_3$; halogen; C$_1$–C$_3$ alkoxy; hydroxy; —NO$_2$; —OCF$_3$; —CONR$^a$R$^b$; COOR$^a$; —COR$^a$; —(CH$_2$)$_{p2}$NR$^a$R$^b$; —(CH$_2$)$_{p3}$CH$_3$, (CH$_2$)$_{p4}$SOR$^a$R$^b$; —(CH$_2$)$_{p5}$SO$_2$R$^a$; —(CH$_2$)$_{p6}$SO$_2$NR$^a$; C$_4$–C$_8$ (alkyl-cycloalkyl) wherein alkyl is C$_1$–C$_2$ alkyl and cycloalkyl is C$_3$–C$_6$ cycloalkyl; 1 or 2 heteroaryl(s) having from 5 to 10 atoms and the heteroatom(s) being selected from any of S, N and O; and oxides such as N-oxides or sulfoxides; and wherein $R^a$ and $R^b$ is each and independently selected from hydrogen, a branched or straight $C_1$–$C_6$ alkyl, $C_1$–$C_6$ alkenyl, $C_3$–$C_8$ cycloalkyl; and wherein p1, p2, p3, p4, p5 and p6 is each and independently 0, 1 or 2.

Within the scope of the invention are also pharmaceutically acceptable salts of the compounds of the formula I, as well as isomers, hydrates, isoforms and prodrugs thereof.

Preferred compounds according to the invention are compounds of the formula I wherein Q is

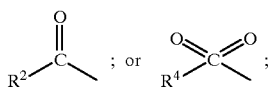

wherein
$R^2$ and $R^4$ is each and independently selected from any of
(i) $C_6$–$C_{10}$ aryl; or
(ii) heteroaryl having from 5 to 10 atoms and the heteroatom being selected from any of S, N and O; and
wherein the aryl and heteroaryl may optionally and independently be substituted by 1 or 2 substituents Y where each Y is as defined above;
(iii) a straight or branched $C_1$–$C_6$ alkyl or $C_2$–$C_6$ alkynyl;
(iv) saturated or unsaturated $C_3$–$C_6$ cycloalkyl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined above;

Particularly preferred compounds according to the invention are compounds of the formula I wherein
$R^1$ is
(i) phenyl optionally and independently be substituted by 1 or 2 substituents Y where each Y is as defined above;
(ii) naphthyl optionally and independently be substituted by 1 or 2 substituents Y where each Y is as defined above;
(iii) heteroaryl having from 5 to 10 atoms and the heteroatom being selected from any of S, N and O; and wherein the aryl and heteroaryl may optionally and independently be substituted by 1 or 2 substituents Y where each Y is as defined above;

Q is

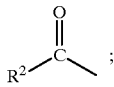

wherein
$R^2$ is
(i) phenyl optionally and independently be substituted by 1 or 2 substituents Y where each Y is as defined above; or
(ii) naphthyl optionally and independently be substituted by 1 or 2 substituents Y where each Y is as defined above.

By "halogen" we mean chloro, fluoro, bromo and iodo.

By "aryl" we mean an aromatic ring having 6 or 10 carbon atoms, such as phenyl and naphthyl.

By "heteroaryl" we mean an aromatic ring in which one or more of the from 5–10 atoms in the ring are elements other than carbon, such as N, S and O.

By "isomers" we mean compounds of the formula I, which differ by the position of their functional group and/or orientation. By "orientation" we mean stereoisomers, diastereoisomers, regioisomers and enantiomers.

By "isoforms" we mean compounds of the formula I which differ in the relative physical arrangement of molecules by crystal lattice, such that isoforms refer to various crystalline compounds and amorphous compounds.

By "prodrug" we mean pharmacologically acceptable derivatives, e.g. esters and amides, such that the resulting biotransformation product of the derivative is an active form of the drug. The reference by Goodman and Gilmans, The Pharmacological basis of Therapeutics, 8th ed., McGraw-Hill, Int. Ed. 1992, "Biotransformation of Drugs, p. 13–15, describing prodrugs generally, is hereby incorporated by reference.

The novel compounds of the present invention are useful in therapy, especially for the treatment of various pain conditions such as chronic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration-or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. Amnesia, analgesia, muscle relaxation and sedation). Included in this combination are inhaled anaesthetics, hypnotica, anxiolytics, neuromuscular blockers and opioids.

The compounds of the present invention in isotopically labelled form are useful as a diagnostic agent.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

The best mode of performing the invention known at present, is to use the compounds according to Example 1 (compound 11), Example 8 (compound 18), Example 9

(compound 19), Example 10 (compound 20) and Example 11 (compound 21). The numbering of the compounds is in accordance with the numbering in the Schemes presented in the following.

Methods of Preparation

The compounds of the present invention may be prepared by following the synthetic routes described in Scheme 1 below.

General Procedure for the Preparation of 1,4 or 1, 3-guanidinomethyl Aminomethyl Xylylene

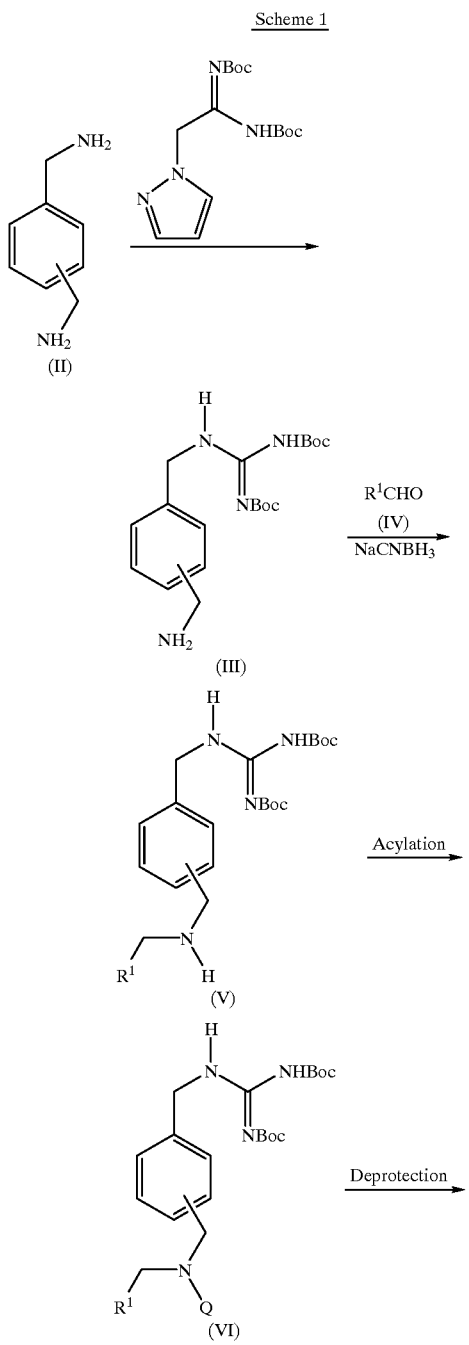

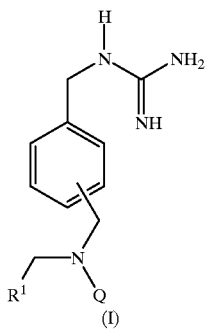

As shown in Scheme 1 above, compounds of the formula I may be obtained from commercially available bis-amino-xylylene (compound II). Compound II is converted into mono-(diBoc)-guanidinomethyl derivative m using a protected guanylating reagent such as 1-H-pyrazole-1-(N,N-bis(tert-butoxycarbonylcarboxamidine) in an organic solvent such as THF.

The secondary amine of the formula V may be generated using a reductive amination step where the compound of the formula III is reacted with an aldehyde (compound IV wherein $R^1$ is as defined in formula I above), in the presence of an acid such as acetic acid or a Lewis acid such as $ZnCl_2$ and in a protic solvent such as methanol or ethanol in the presence of a reducing agent such as sodium cyanoborohydride.

Compounds of the formula VI may be obtained by performing an acylating reaction where compound V is mixed with an acid chloride or other appropriate acylating reagent such as an acid anhydride in a solvent such as methylene chloride and in the presence of a tertiary amine as base, such as triethylamine.

Finally, compounds of the formula I may be obtained by cleavage of the Boc protecting group with an acid such as aqueous hydrochloric acid or by using organic acid such as trifluoroacetic acid in a solvent such as methylene chloride.

In the formulas of Scheme 1 above, $R^1$ and Q are as defined in formula I above.

EXAMPLES

The invention will now be described in more detail by way of the following Examples, which are not to be construed as limiting the invention in any way.

Step 1(a)

Preparation of 1-(diBoc)-guanidinomethyl-4-aminomethyl Benzene (compound 2)

Part A

1-H-pyrazole-1-carboxamidine was prepared according to Bernatowicz et.al., J. Org. Chem. 1992, 57, pp.2497–2502, and protected with di-tert-butyl dicarbonate to give 1-H-pyrazole-1-N,N-bis(tert-butoxycarbonyl) carboxamidine according to Drake et.al, Synth. 1994. pp.579–582.

Part B

To a solution of p-xylylenediamine (30.8 g, 0.226 mol) in THF (300 mL) was added a solution of 1-H-Pyrazole-1-(N, N-bis(tert-butoxycarbonyl)carboxamidine (35.0 g, 0.113 mol) in THF (100 mL). The solution was stirred at room temperature for 3 h. The solvent was removed under reduced pressure. Water was added to the residue and the aqueous mixture was extracted with ethyl acetate. The organic layer was washed with brine, dried over MgSO$_4$ and concentrated. The product (compound 2) was purified by column chromatography on silica gel using a mixture of methylene chloride:methanol as the eluent to give 24.3 g (57% yield) of 1-(diBoc)-guanidinomethyl-4-aminomethyl benzene.

$^1$H NMR (CDC13) δ 8.5 (broad s, 1H), 7.32 (s, 4H), 4.65 (d, 2H), 3.89 (s, 2H), 1.5 (s, 9H), 1.48 (s, 9H).

Step 1(b)

Preparation of 1-(diBoc)-guanidinomethyl-3-aminomethyl Benzene (compound 3)

1-(diBoc)-guanidinomethyl-3-aminomethyl benzene (compound 3) was prepared in a similar fashion from m-xylylenediamine and of 1-H-Pyrazole-1-(N,N-bis(tert-butoxycarbonyl)carboxamidine.

$^1$H NMR (CDC13) δ 8.52 (broad s, 1H), 7.28–7.08 (m, 4H), 4.56 (d, 2H), 3.81 (s, 2H), 1.42 (s, 9H), 1.39 (s, 9H).

Step 2

Reductive Amination—preparation of 1-(diBoc)-guanidinomethyl-4-[N-(benzyl)-aminomethyl]benzene (compound 3)

To a methanolic solution (15 ml) of compound 2 (322 mg, 0.85 mol) and diphenylacetaldehyde (183.7 mg, 0.94 mol) was added zinc chloride (127.5 mg, 0.94 mmol) and sodium cyanoborohydride (64.2 mg, 1.02 mol). The mixture was stirred over night under nitrogen, wherafter the mixture was diluted with saturated aqueous sodium bicarbonate and extracted with methylene chloride. The organic phase was washed with brine, dried over MgSO$_4$ and concentrated. This crude product was further purified by silica gel chromatography using CH$_2$Cl$_2$/MeOH (95:5) as the solvent, to give 145 mg of the pure desired product (compound 3).

Specific examples illustrating the preparation of secondary amines, i.e. intermediates of the general formula V, are provided in Table 1 below.

TABLE 1

| Intermediate compound no. | Intermediate compound of the general fomula V of Scheme 1 and the chemical name therefore | Characterization data |
|---|---|---|
| 3 | [structure] 1-(diBoc)-guanidinomethyl-4-[N-(2,2-diphenylethyl)aminomethyl] benzene | $^1$H NMR (CDCl$_3$) δ 8.5(broad s, 1H), 7.23–7.14(m, 14H), 4.58(d, 2H), 4.18(t, 1H), 3.78(s, 2H), 3.22(d, 2H), 1.50(s, 9H), 1.47(s, 9H). MS(FAB+): 559(M + H), 359. |
| 4 | [structure] 1-(diBoc)-guanidinomethyl-4-[N-(4-chlorobenzyl)aminomethyl] benzene | $^1$H NMR (DMSO-d$_6$) δ 8.6(broad t, 1H), 7.42–7.1(m, 10H), 4.52(t, 2H), 3.7(s, 2H), 3.2(s, 2H), 1.5(s, 9H), 1.45(s, 9H). MS(FAB+): 503(M + H), 403, 303. |
| 5 | [structure] 1-(diBoc)-guanidinomethyl-4-[N-(benzyl)aminomethyl] benzene | $^1$H NMR (CDCl$_3$) δ 7.2(m, 9H), 4.5(s, 2H), 4.15(t, 2H), 3.7(s, 2H), 1.5(s, 18H). |
| 6 | [structure] 1-(diBoc)-guanidinomethyl-4-[N-(2-chlorobenzyl)aminomethyl] benzene | $^1$H NMR (CDCl$_3$) δ 8.62(broad s, 1H), 7.48–7.1(m, 8H), 4.62(d, 2H), 3.95(s, 2H), 3.85(s, 2H), 1.53(s, 9H), 1.5(s,9H). |

TABLE 1-continued

| Intermediate compound no. | Intermediate compound of the general formula V of Scheme 1 and the chemical name therefore | Characterization data |
|---|---|---|
| 7 | 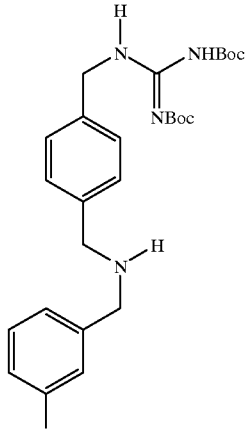<br>1-(diBoc)-guanidinomethyl-4-[N-(3-chlorobenzyl)aminomethyl] benzene | $^1$H NMR (CDCl$_3$) δ 8.56(broad t, 1H), 7.4–7.15(m, 8H), 4.6(d, 2H), 3.8(s, 4H), 1.56(s, 9H), 1.52(s, 9H). MS(APCI): 503(M + H), 403, 303. |
| 8 | 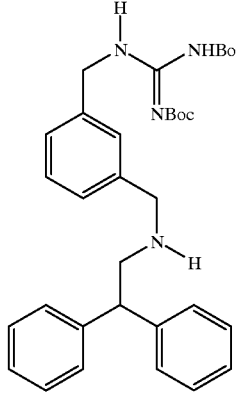<br>1-(diBoc)-guanidinomethyl-3-[N-(2,2-diphenylethyl)aminomethyl] benzene | MS(ES+): 559(M + H), 459, 359. |
| 9 | 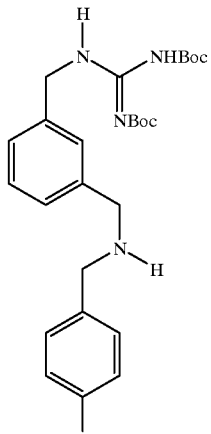<br>1-(diBoc)-guanidinomethyl-3-[N-(4-chlorobenzyl)aminomethyl] benzene | $^1$H NMR (CDCl$_3$) δ 8.48(broad s, 1H), 7.3–6.96(m, 8H), 4.68–4.32(m, 4H), 3.78–3.6(m, 2H). |

Example 1

Preparation of 4-N-(benzoyl)-N-(2,2-diphenylethyl)aminomethyl-1-guanidinomethyl-p-xylylene (compound 11)

Compound 11 of this Example was prepared by following the reaction procedure described in Scheme 2 below.

Scheme 2

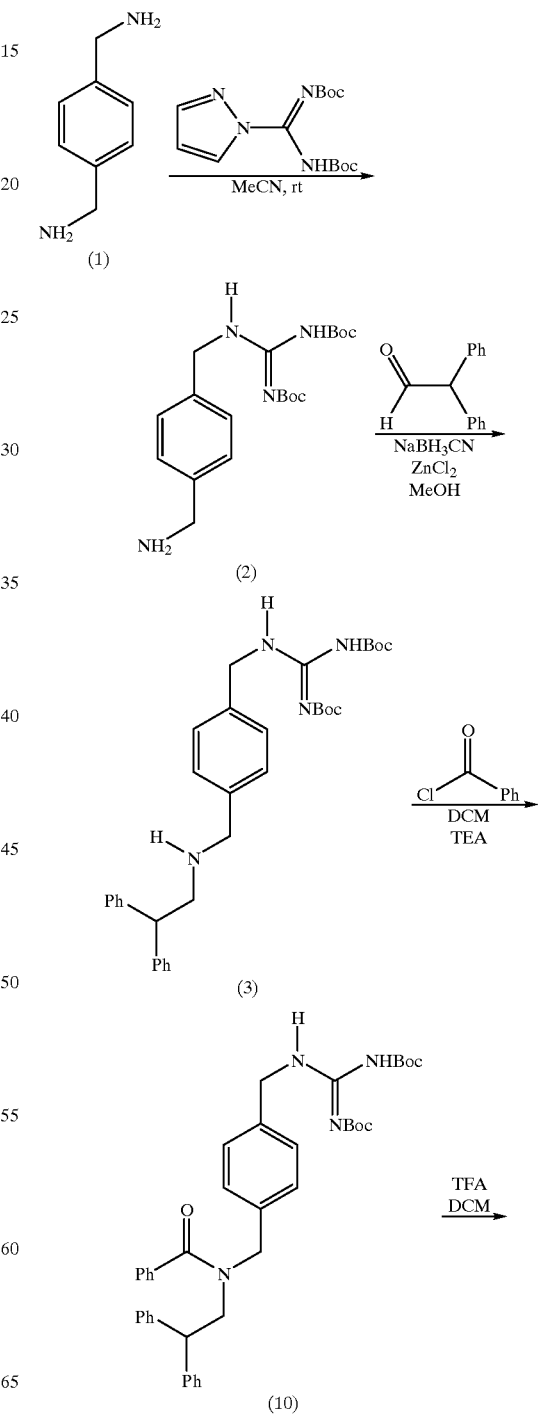

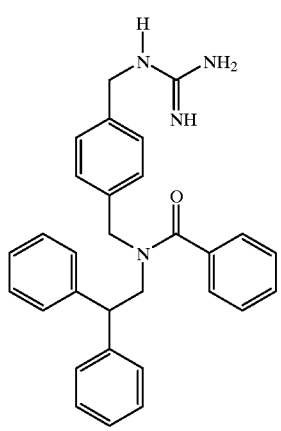

Example 1
Compound 11

To a solution of compound 3 (145 mg, 0.26 mol) in methylene chloride (10 ml) was added benzoyl chloride (2.96 mg, 0.52 mol) and triethylamine (52.52 mg, 0.52 mmol). The mixture was stirred at room temperature for 2 h, washed with saturated $NH_4Cl$ (aq) and brine, dried over $MgSO_4$ and concentrated to give the crude product (compound 10). This crude compound was used directly without purification for the preparation of compound 11. It was dissolved in dry methylene chloride (3 ml), 1.5 ml of TFA was added and the reaction mixture was stirred at room temperature for 1 hour. The excess of solvent and TFA was evaporated, the residue was purified by reverse phase preparative HPLC to give the pure desired product (100 mg, 84%) (compound 11).

$^1$H NMR (DMSO-$d_6$) δ 7.24–6.75 (m, 19H), 4.50–3.42 (m, 7H).

MS: 463.07 (M+H).

Examples 2–6

The following compounds were prepared by using the same procedure as described in Example 1, but using the intermediate and the reagent indicated in Table 2 below.

TABLE 2

| Ex | Structure and chemical name | Intermediate used | Reagent | Physical Characterization |
|---|---|---|---|---|
| 2 | (12) 4-N-(1-Naphthoyl)-N-(4-chlorobenzyl)-aminomethyl-1-guanidinomethyl-p-xylene | 4 | 1-napthoyl chloride | $^1$H NMR (DMSO-$d_6$) δ 8.6(broad, 1H), 7.9(s, 1H), 7.55–7.1(m, 14H), 4.6(broad, 4H), 4.3(d, 2H). |
| 3 | (13) | 3 | 2,6-dichloro-benzoyl-chloride | $^1$H NMR (DMSO-$d_6$) δ 7.5–7.1(m, 17H), 4.55(t, 1H), 4.35(d, 2H), 4.1(d, 4H). |

TABLE 2-continued

| Ex | Structure and chemical name | Intermediate used | Reagent | Physical Characterization |
|---|---|---|---|---|
| | 4-N-(2,6-dichlorobenzoyl)-N-(2,2-diphenylethyl)-aminomethyl-1-guanidinomethyl-p-xylene | | | |
| 4 | (14) 4-N-(2,6-dichlorobenzoyl)-N-(2,2-diphenylethyl)-aminomethyl-1-guanidino methyl-p-xylylene | 3 | 2,6-dimethoxy-benzoyl chloride | $^1$H NMR (DMSO-d$_6$) δ 7.5–7.2(m, 7H), 7.05(d, 6H), 6.75(d, 2H), 6.55(d, 2H), 4.55(t, 1H), 4.40(m, 4H), 4.35(d, 2H), 3.8(s, 6H). |
| 5 | (15) 3-N-(2,6-dichlorobenzoyl)-N-(2,2-diphenylethyl)-aminomethyl-1-guanidinomethyl-m-xylylene | 8 | 2,6-dichloro-benzoyl-chloride | $^1$H NMR (DMSO-d$_6$) δ 8.0(broad, 1H), 7.5–7.0(m, 17H), 4.7(t, 1H), 4.55(d, 1H), 4.45(d, 1H), 4.3–4.1(m, 4H). |
| 6 | (16) 3-N-(2-naphtoyl)-N-(4-chlorobenzyl)-aminomethyl-1-guanidinomethyl-m-xylylene | 10 | benzoyl chloride | $^1$H NMR (COCl$_3$) δ9.9(broad, 1H); 8.6(broad, 1H), .9–8.05(m, 4H); 7.55(m, 3H), 7.2–7.4(m, 10H), 4.6(broad, 4H), 4.4(d, 2H). |

TABLE 2-continued

| Ex | Structure and chemical name | Intermediate used | Reagent | Physical Characterization |
|---|---|---|---|---|
| 7 | 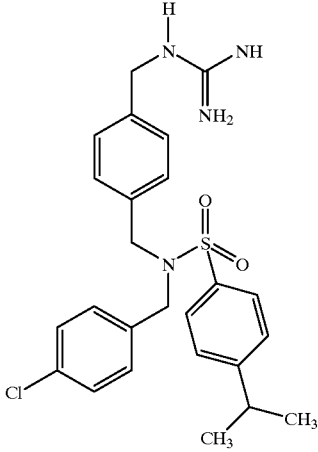<br>(17)<br>4-N-(4-isopropylphenylsulfonyl)-<br>N-(4-dichlorobenzyl)-<br>aminomethyl-1-<br>guanidinomethyl-p-xylylene | 5 | isopropyl-phenyl sulphonyl-chloride | $^1$H NMR (DMSO-$d_6$) δ8.0(broad, 1H), 7.9(d, 2H), 7.5(d, 2H), 7.3–7.0(m, 8H), 4.3(broad d, 6H), 3.05(m, 1H), 1.25(d, 6H). MS(APCI): 485. (M + H). |

Examples 8–11

The following compounds were prepared by following the synthetic route described in Scheme 3 below.

Scheme 3

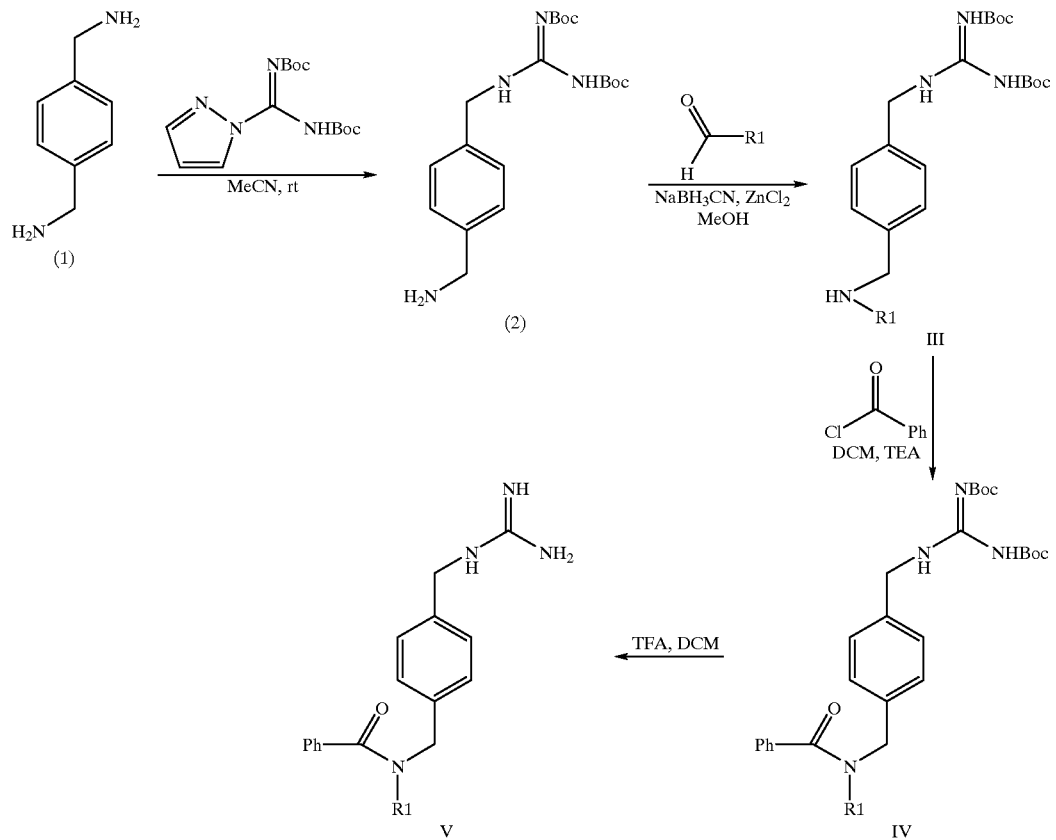

General Procedure

Compound 1 (commercially available) is converted into mono-(diBoc)-guanidinomethyl derivative2 using a protected guanylating reagent such as 1-H-pyrazole-1-(N,N-bis(tert-butoxycarbonyl)carboxamidine in an organic solvent such as THF.

The secondary amine of the formula III may be generated using a reductive amination step, where compound 2 is reacted with an aldehyde II in the presence of an acid such as acetic acid or a Lewis acid such as ZnCl2, in a protic solvent such as methanol or ethanol in the presence of a reducing agent such as sodium cyanobrohydride.

Compounds of the formula IV may be obtained by performing an acetylation using compound III with the benzoylchloride in a solvent such as methylene chloride and in the presence of a tertiary amine as base, such as triethylamine.

Finally, a compound of formula V may be obtained by cleavage of the Boc protecting group with an acide such as aqueous hydrochloric acid or by using organic acid such as trifluoroacetic acid in a solvent such as a methylene chloride.

Example 8
Preparation of N-[4-({[amino(imino)methyl]amino}methyl)benzyl-N-(1-naphtylmethyl)benzamide (compound 18)

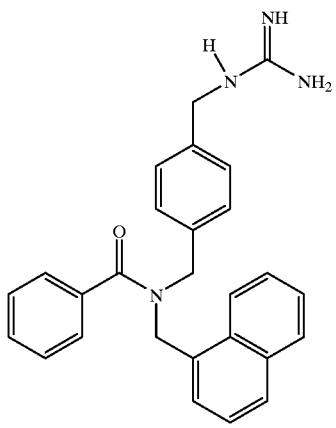
(18)

To a methanolic solution(15 ml) of compound 2(100 mg, 0.264 mmol) and 1-Naphathylaldehyde(41 mg, 0.264 mmol) was added zinc chloride(35.97 mg, 0.264 mmol) and sodium cyanoborohydride(18.25 mg, 0.29 mmol). The mixture was stirred over night under nitrogen. Then the mixture was diluted with saturated aqueous sodium bicarbonate and extracted with methylene chloride. The organic phase was washed with brine, dried over MgSO$_4$ and concentrated. This crude product was further purified by silica gel chromatography using CH$_2$Cl$_2$/MeOH (95:5) as the solvent to give 50 mg of the pure desired product (compound 3 of formula III).

Preparation of Compound 4 & 5

To a solution of compound 3(50 mg, 0.096 mmol) in methylene chloride(10 ml) was added benzoylchloride (27 mg, 0.192 mmol) and triethylamine(19 mg, 0.192 mmol). The mixture was stirred at room temperature for 2 h., washed with saturated NH$_4$Cl aqueous solution and brine, dried over MgSO$_4$ and concentrated to give the crude product(compound 4 of formula IV). This crude compound was used directly without purification for the preparation of compound 5 of formula V. It was dissolved in dry methylene chloride(3 ml), 1.5 ml of TFA was added and the reaction mixture was stirred at rt for 1 h. The excess of solvent and TFA was evaporated, the residue was purified by reverse phase preparative HPLC to give the pure desired product (47 mg).

HPLC: >99% (215 nm), >99% (254 nm)

M.S.: Calc. 423.53 (MH+), Observed 423.50 (MH+)

Example 9

Preparation of N-[4-({[amino(imino)methyl]amino}methyl)benzyl-N-(3-methyl-1-benzothiophen-2-yl)methyl)benzamide (compound 19)

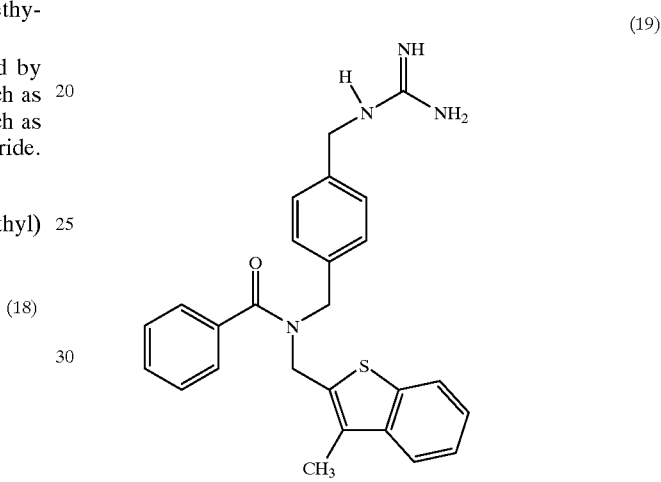
(19)

Compound 19 was prepared by following the synthetic procedure as described for Example 8 (compound 18). The reagent used was benzoyl chloride, and the intermediate used was

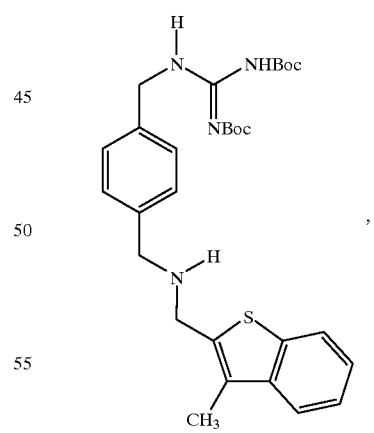

prepared in a way analogous to intermediate no. 4 above, but using 3-methylthiophene-2-carboxaldehyde instead of 4-chlorobenzaldehyde.

Physical Characterization for Compound 19:

HPLC: >99% (215 nm), >99% (254 nm)

M.S.: Calc. 443.59 (MH+), Observed 443.45 (MH+)

Example 10

Preparation of N-[4-({[amino(imino)methyl]amino}methyl)benzyl-N-(3-fluorobenzyl)benzamide (compound 20)

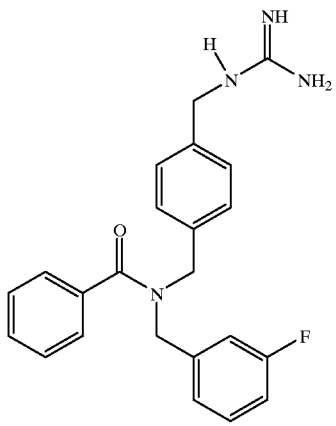

(20)

Compound 20 was prepared by following the synthetic procedure as described for Example 8 (compound 18). The reagent used was benzoyl chloride, and the intermediate used was

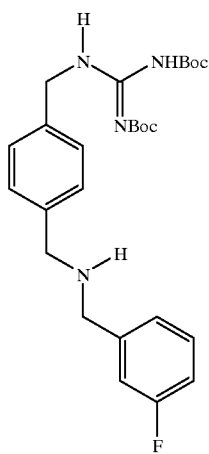

prepared in a way analogous to intermediate no. 4 above, but using 3-fluoro benzaldehyde instead of 4-chlorobenzaldehyde.

Physical Characterization for Compound 20:

HPLC: >99% (215 nm), >99% (254 nm)
M.S.: Calc. 391.46 (MH+), Observed 391.44 (MH+)

Example 11

Preparation of N-[4-({[amino(imino)methyl]amino}methyl)benzyl-N-(2,6-dichlorobenzyl)benzamide (compound 21)

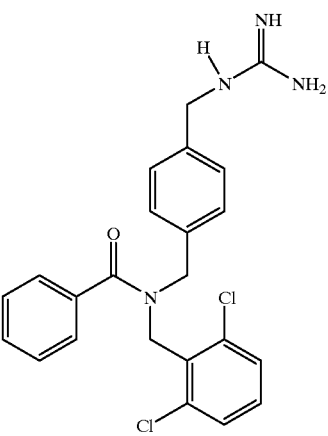

(21)

Compound 21 was prepared by following the synthetic procedure as described for Example 8 (compound 18). The reagent used was benzoyl chloride, and the intermediate used was

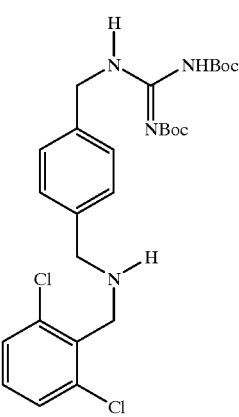

prepared in a way analogous to intermediate no. 4 above, but using 2,6-dichloro benzaldehyde instead of 4-chlorobenzaldehyde.

Physical Characterization for Compound 21:

HPLC: >99% (215 nm), >99% (254 nm)
M.S.: Calc. 442.36 (MH+), Observed 441.37, 443.39 (M+2)

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglurnine, procaine, aluminium, calcium, lithium, magnesium, potassium, sodium, and zinc.

Preferred pharmaceutically acceptable salts are the hydrochlorides, trifluoroacetates and bitartrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

A) IN VITRO MODEL

Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for pg protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 MM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasable). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one-site model.

B) BIOLOGICAL MODEL (IN VIVO MODEL) FREUND'S COMPLETE ADJUVANT (FCA), AND SCIATIC NERVE CUFF INDUCED MECHANO-ALLODYNIA IN RAT

Animals

Male Sprague-Dawley rats (Charles River, St-Constant, Canada) weighing 175–200 g at the time of surgery were used. They were housed in groups of three in rooms thermostatically maintained at 20° C. with a 12:12 hr light/dark cycle, and with free access to food and water. After arrival, the animals were allowed to acclimatize for at least 2 days before surgery. The experiments were approved by the appropriate Medical Ethical Committee for animal studies.

EXPERIMENTAL PROCEDURE
FREUND'S COMPLETE ADJUVANT

The rats were first anesthetized in a Halothane chamber after which 10 µl of FCA was injected s.c. into the dorsal region of the left foot, between the second and third external digits. The animals were then allowed to recover from anesthesia under observation in their home cage.

SCIATIC NERVE CUFF

The animals were prepared according to the method described by Mosconi and Kruger (1996). Rats were anesthetized with a mixture of Ketamine/Xylazine i.p. (2 ml/kg) and placed on their right side and an incision made over, and along the axis of, the lateral aspect of the left femur. The muscles of the upper quadriceps were teased apart to reveal the sciatic nerve on which a plastic cuff (PE-60 tubing, 2 mm long) was placed around. The wound was then closed in two layers with 3-0 vicryl and silk sutures.

DETERMINATION OF MECHANO-ALLODYNIA USING VON FREY TESTING

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

TESTING PROTOCOL

The animals were tested on postoperative day 1 for the FCA-treated group and on post-operative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold}=10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \, MPE = \frac{\text{Drug treated threshold (g)} - \text{allodynia threshold(g)}}{\text{Control threshold (g)} - \text{allodynia threshold (g)}} \times 100$$

ADMINISTRATION OF TEST SUBSTANCE

Rats were injected (subcutaneously, intraperitoneally, or orally) with a test substance prior to von Frey testing, the time between administration of test compound and the von Frey test varied depending upon the nature of the test compound.

What is claimed is:

1. A compound according to formula I

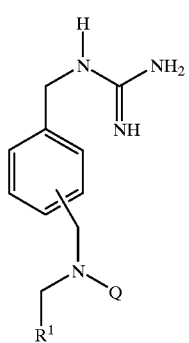

wherein $R^1$ is selected from any one of
(i) a straight or branched $C_1$–$C_6$ alky, $C_2$–$C_6$ alkenyl or $C_2$–$C_6$ alkynyl, where each alkyl, alkenyl or alkynyl may optionally be substituted by one or more aromatic or heteroaromatic substituents;
(ii) $C_3$–$C_7$ cycloalkyl optionally substituted by any one of $C_1$–$C_6$ alkyl, $C_1$–$C_6$ alkoxy, or hydroxy;
(iii) hydrogen, halogen or $C_1$–$C_6$ alkoxy;
(iv) $C_6$–$C_{10}$ aryl;
(v) heteroaryl having from 5 to 10 atoms, each heteroatom being selected from any of S, N and O;

wherein the aryl and heteroaryl may optionally and independently be substituted by 1 or 2 substituents Y wherein each Y is as defined below;

Q is selected from any of CH$_3$;

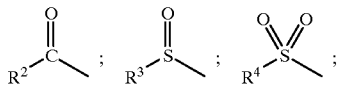

wherein

R$^2$, R$^3$ and R$^4$ are each and independently selected from any of
(i) C$_6$–C$_{10}$ aryl; or
(ii) heteroaryl having from 5 to 10 atoms, each heteroatom being selected from any of S, N and O; and wherein the aryl and heteroaryl may optionally and independently be substituted by 1 or 2 substituents Y where each Y is as defined below;
(iii) hydrogen;
(iv) a straight or branched C$_1$–C$_6$ alkyl, C$_2$–C$_6$ alkenyl or C$_2$–C$_6$ alkynyl;
(v) saturated or unsaturated C$_3$–C$_{10}$ cycloalkyl, optionally and independently substituted by one or more heteroaryls having from 5 to 10 atoms, each heteroatom being selected from any of S, N and O and wherein the heteroaryl may optionally and independently be substituted by 1 or 2 substituents Y wherein each Y is as defined below;
Y is each and independently selected from any of hydrogen, CH$_3$; —(CH$_2$)$_{p1}$CF$_3$; halogen; C$_1$–C$_3$ alkoxy; hydroxy; —NO$_2$; —OCF$_3$; —CONR$^a$R$^b$; —COOR$^a$; —COR$^a$; —(CH$_2$)$_{p2}$NR$^a$R$^b$; —(CH$_2$)$_{p3}$CH$_3$; (CH$_2$)$_{p4}$SOR$^a$R$^b$; —(CH$_2$)$_{p5}$SO$_2$R$^a$; —(CH$_2$)$_{p6}$SO$_2$NR$^a$; C$_4$–C$_8$ (alkyl-cycloalkyl) wherein alkyl is C$_1$–C$_2$ alkyl and cycloalkyl is C$_3$–C$_6$ cycloalkyl; 1 or 2 heteroaryls having from 5 to 10 atoms, each heteroatom being selected from any of S, N and O; and oxides; and wherein
R$^a$ and R$^b$ are each and independently selected from hydrogen, a branched or straight C$_1$–C$_6$ alkyl, C$_1$–C$_6$ alkenyl, C$_3$–C$_8$ cycloalkyl; and wherein p1, p2, p3, p4, p5 and p6 are each and independently 0, 1 or 2;

or a pharmaceutically acceptable salt thereof.

2. A compound according to formula I of claim 1, wherein Q is

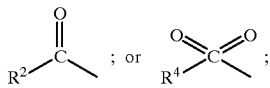

wherein
R$^2$ and R$^4$ is each and independently selected from any of
(i) C$_6$–C$_{10}$ aryl; or
(ii) heteroaryl having from 5 to 10 atoms and the heteroatom being selected from any of S, N and O; and wherein the aryl and heteroaryl may optionally and independently be substituted by 1 or 2 substituents Y where each Y is as defined in claim 1;
(iii) a straight or branched C$_1$–C$_6$ alkyl or C$_2$–C$_6$ alkynyl;
(iv) saturated or unsaturated C$_3$–C$_6$ cycloalkyl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined in claim 1.

3. A compound according to claim 2, wherein
R$^1$ is
(i) phenyl optionally and independently be substituted by 1 or 2 substituents Y where each Y is as defined in claim 1;
(ii) naphthyl optionally and independently be substituted by 1 or 2 substituents Y where each Y is as defined in claim 1;
(iii) heteroaryl having from 5 to 10 atoms and the heteroatom being selected from any of S, N and O; and wherein the aryl and heteroaryl may optionally and independently be substituted by 1 or 2 substituents Y where each Y is as defined in claim 1;

Q is

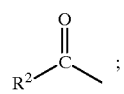

wherein
R$^2$ is
(i) phenyl optionally and independently be substituted by 1 or 2 substituents Y where each Y is as defined in claim 1; or
(ii) naphthyl optionally and independently be substituted by 1 or 2 substituents Y where each Y is as defined in claim 1.

4. A compound according to any of the previous claims, which compound is anyone selected from

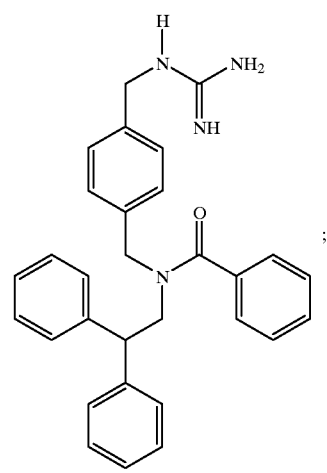

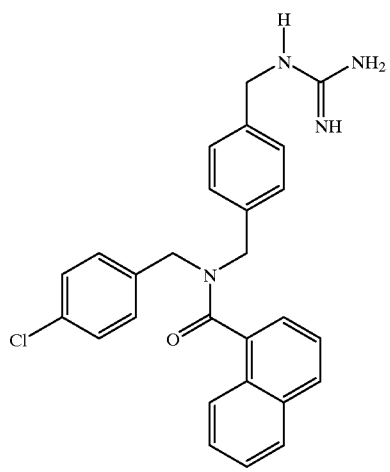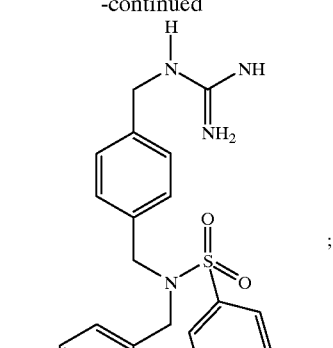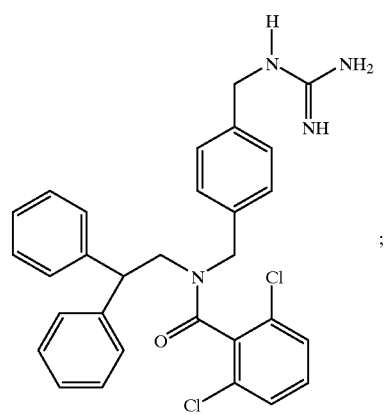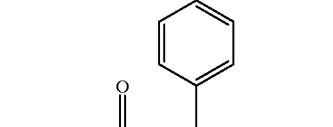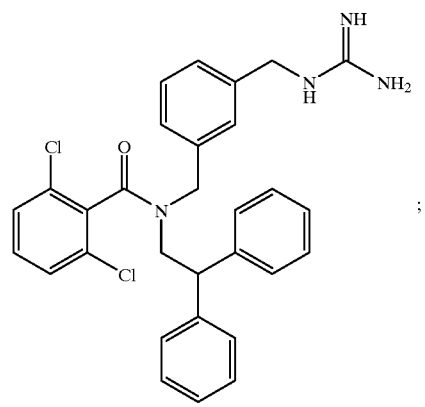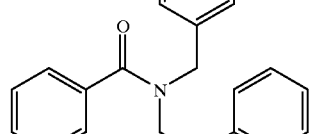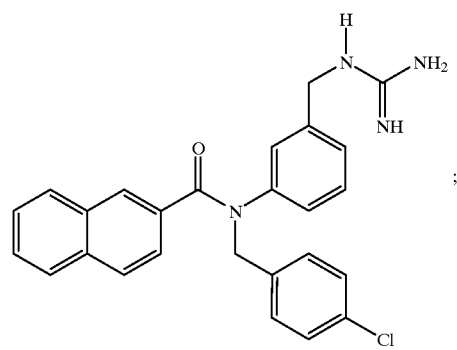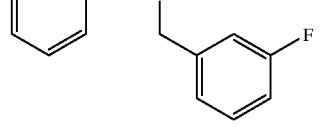

-continued

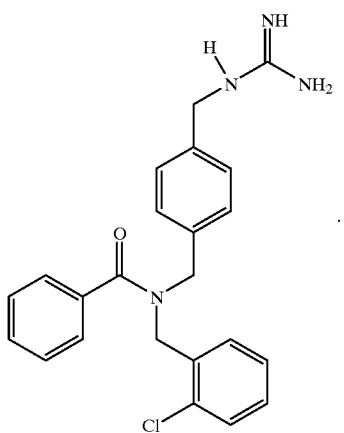

5. A compound according to any one of the preceding claims, wherein said compound is in the form of a hydrochloride, sulfate, tartrate or citrate salt.

6. A compound according to any one of claims 1–4, wherein said compound is isotopically labeled.

7. A pharmaceutical composition comprising a compound of formula I according to claim 1 as an active ingredient, together with a pharmacologically and pharmaceutically acceptable carrier.

8. A method for the treatment of a patient for pain, wherein an effective amount of a compound of formula I according to claim 1 is administered to said patient.

9. A method for the treatment of a patient for a gastrointestinal disorder, wherein an effective amount of a compound of formula I according to claim 1, is administered to said patient.

10. A method for the treatment of a patient for a spinal injury, wherein an effective amount of a compound of formula I according to claim 1, is administered to said patient.

* * * * *